United States Patent [19]

Schulte et al.

[11] Patent Number: 4,560,353
[45] Date of Patent: Dec. 24, 1985

[54] TOOTH IMPLANT

[75] Inventors: Willi Schulte, Tübingen; Günther Heimke, Weinheim, both of Fed. Rep. of Germany

[73] Assignee: Friedrichsfeld GmbH - Steinzeug- und Kunststoffwerke, Mannheim, Fed. Rep. of Germany

[21] Appl. No.: 514,787

[22] Filed: Jul. 18, 1983
(Under 37 CFR 1.47)

[30] Foreign Application Priority Data

Jul. 17, 1982 [DE] Fed. Rep. of Germany ....... 3226831

[51] Int. Cl.[4] .............................................. A61C 8/00
[52] U.S. Cl. ..................................... 433/173; 433/176
[58] Field of Search ................ 433/173, 175, 176, 201, 433/220, 221, 174

[56] References Cited

U.S. PATENT DOCUMENTS

| 3,849,887 | 11/1974 | Brainin | 433/201 |
|---|---|---|---|
| 3,950,850 | 4/1976 | Driskell et al. | 433/173 |
| 3,992,780 | 11/1976 | Herskovits | 433/176 |
| 4,185,383 | 1/1980 | Heimke et al. | 433/173 |
| 4,293,302 | 10/1981 | Hassler et al. | 433/173 |
| 4,302,188 | 11/1981 | Driskell | 433/173 |

FOREIGN PATENT DOCUMENTS

| 2628929 | 1/1977 | Fed. Rep. of Germany | 433/173 |
|---|---|---|---|
| 7900461 | 6/1979 | Fed. Rep. of Germany | 433/173 |
| 2853638 | 6/1979 | Fed. Rep. of Germany | 433/176 |
| 2412302 | 8/1979 | France | 433/173 |

Primary Examiner—John J. Wilson
Attorney, Agent, or Firm—Fisher, Christen & Sabol

[57] ABSTRACT

Implants made of corrosion resistant metals such as titanium, tantalum or niobium, wherein the parts to be inserted into the jaw bone have an essentially leaf-shaped form, and the parts projecting from the jaw bone right through into the mouth cavity being a crown, bridge or some other superstructure, have the problem that such implants have frequently been surrounded by a soft tissue fringe as a result of which the implants are merely loosely anchored in the jaw bone. This also causes an irritation of mucous membrane in the region of the implant part extending through the mucous membrane, as a result of which the implant's bacteria-tight closure is no longer present in many instances. There is an annular groove on the outside of the ring. In order to hold the implant during the healing-in phase with a certainty of freedom from any load, the elements of the superstructure are attached to the post penetrating the mucous membrane by means of a blind hole.

14 Claims, 3 Drawing Figures

TOOTH IMPLANT

BACKGROUND OF THE INVENTION

1. Field of the Invention

The invention relates to a metal implant which is corrosion resistant in the body.

2. Prior Art

An implant constructed of a metal, such as, titanium, tantalum or niobium, which is corrosion resistant in the body and consists essentially of (a) a leaf-shaped part to be inserted into the jaw bone, (b) a post-like part leading from the jaw bone through the mucous membrane into the mouth cavity, and (c) means for attaching the crown, bridge or some other superstructure, provided at the end of the post-like part pointing into the mouth cavity, is known.

Such implants have recently been described in German OS No. 2,853,638. Such leaf implants have previously preferably been inserted in the lateral tooth area for the attachment of total or partial tooth protheses in jaw bones. The rate of success for such implants, i.e., their staying time in the jaw until the necessity for removal of such implants, amounts up to about 50 percent after five years. This high loss-rate rests essentially on the cooperation of two factors, the negative influences of which reinforce each other. For one thing, implants of such prior form are not surrounded directly by the bone tissue, but rather a close attachment of the bony tissue of such implants with a layer of soft tissue occurs, which separates the implants from the real bone bed. This occurs because the implants do not have sufficiently large surfaces, thereby not transferring the chewing forces in the form of a pure pressure load to the bone.

Therefore, relative movement between the adjacent tissues and the surface of the implant always occurs at the surfaces of such implants, which leads to the previously-mentioned binding tissue layer. Accordingly such implants are not anchored firmly in the bone, and they are rather capable of carrying out at least small movement relative to the jaw bone, which is spring-cushioned by the fringe of soft tissue.

Secondly, only metal parts have been provided on such implants in the area thereof extending through the mucous membrane. Moreover, the mucous membrane tissue only conditionally contacts in a bacteria-tight manner on such metal parts. This is related to the fact that even highly corrosion resistant metals, such as, titanium, tantalum or niobium, even in the case of only slight damage of the surface, as might occur again and again during chewing as a result of food components sliding down, release metal ions to the surroundings. The corrosion resistance of these metals in the body medium is due to the formation of dense oxide layers on the surface, which sufficiently avoids the start of dissolution of the very base metals themselves, but only as long as such oxide layers remain undamaged. The metal ions which temporarily start to dissolve after damage to these oxide layers influence the activity of the cells in the immediate surroundings. This leads to irritation of the tissue in the area of the highly sensitive ends of mucous membrane, which upon addition of more unfavorable effects may lead to a penetration by and growth of the bacteria in the depth of the gingiva propria or the epithelium of the gingiva propria. This in turn has, as a consequence, a formation of pockets of soft tissue of fairly large size around the neck of the implant.

The shaking amplitude of the implants which, as mentioned above, are merely surrounded by a soft binding tissue, must be considered as a very important factor which considerably magnifies such irritation of the mucous membrane tissue in the neck area. Since such implants are not firmly anchored in the bone, they carry out separate movement relative to the jaw in their soft tissue bed, for example, in the case of the loads occurring during chewing and above all also during the loads caused by the tongue, which are brought about by the act of swallowing, as a result of which the end of the mucous membrane is subjected to loads or pressure in a completely unphysiological manner.

Beyond that, leaf implants of the previously-used form have a part on the post-shaped part, projecting into the mouth cavity for the attachment of a bridge or superstructure, which extends way above the mucous membrane level. The consequence of this is that such leaf implants cannot be sufficiently protected against loads during the healing-in phase. Such loads during the healing-in phase however, promote the development of the soft tissue fringe, which has been mentioned above.

BROAD DESCRIPTION OF THE INVENTION

The main object of the invention is, therefore, to find a remedy against the above-described combined effect of metal irritation in the area of the end of the mucous membrane and of the moveability of the implant as a result of the soft tissue wrapping. The main object of the invention thus is also to create an implant with which any irritation of the tissue by emerging metal ions in the area where the implant extends through the mucous membrane is definitively avoided, which is not separated from the jaw bone by a soft tissue fringe and which is thus separated from the bony surroundings, but which may be osteo-integrated directly in a bony manner, i.e., may be osteo-integrated without an intermediate tissue layer. Other objects and advantages of the invention are set out herein or are obvious hereto to one ordinarily skilled in the art.

The objects and advantages of the invention are achieved by the implant of the invention.

The main object of the invention is achieved by the invention implant which has a leaf-shaped part which has steps. The step surfaces are disposed away from the post-like part of the implant, thereby pointing into the jaw bone. The part of the post-like part which extends through the mucous membrane is cylindrical, and has therearound a ring of bioinert ceramics, which on its outside has an annular groove. The means for attaching a crown, bridge or superstructure consists of a pocket hole disposed in the post-like part. The opening of the pocket hole is in the top surface of the post-like part above the mucous membrane.

A further feature of the invention is that the leaf-shaped part has perforations, the limiting surfaces of which are oriented perpendicularly to the plane of the leaf. The purely pressure-transmitting surface in the perforations can still be magnified by the facts that the perforations have a rectangular cross section and that two parallel rectangle sides are oriented in parallel to the step surfaces.

A particularly favorable, bacteria-tight closure in the area between the post-like part and the ring made of bioinert ceramics is ensured when the connection between the post-like part and the ring has been produced from bioinert ceramics by active soldering. The lasting and bacteria-tight adaption of the mucous membrane in the area of the implant extending therethrough can be still further improved when the surface of the ceramics is polished in the area of the annular groove. The ring of bioinert ceramics preferably consists of a dense aluminum oxide ceramic.

An additional effect supporting the settling down on the bone tissue, similar to that in the perforation mentioned in leaf-shaped part, can be achieved by lacuna-like indentations.

The attachment of the pressure-transmitting surfaces to the body of the implant has for a consequence that, in the case of the load as a result of chewing pressure, no relative movement can occur along these surfaces. This is so since the bone tissue in the case of such loads is shoved only onto this border surface or, in the case of release, is somewhat dilated, but does not carry out tangential movements in relation to the surface.

At the perpendicular surfaces of the implant thereto, because of the different rigidity of the implant body and the surrounding, essentially spongy bone tissue, in the case of a load, a slight relative movement occurs which brings along the danger of a soft tissue separation in the sense of a border surface pseudo-darthrosis. There one may only count upon a good, direct and thus also load-transmitting bone contact only along the step surfaces. These expectations can be proved to be correct hitherto after long years of continuous examinations in stepped round implants of ceramics. This can be achieved among other way by the fact that such steps—which, when viewed from the direction of the mouth cavity into the jaw, indeed become narrower and narrower—can be cut down by a correspondingly stepped milling cutter having exactly the dimensions of the implant. After insertion of the implant therefore there exists initially already a close bone contact. The bone tissue at these places no longer needs to renew itself any more but only needs to adapt itself correspondingly to the load situation, which has been changed locally by insertion of the implant.

In the area of the extension through of the mucous membrane, the ring of bioinert ceramics ensures with certainty that no ions can start to go into solution, which could irritate the sensitive cells in this area. Such bioinert ceramic consists entirely and throughout of metal oxides, therefore, its surface cannot be damaged by food remnants sliding down in such a way that plain metal may temporarily be exposed and in contact with the tissue and accordingly discharge ions. In the inert oxides in question, in which the word "inert" is inherent, the metal ions are so firmly bound that they cannot start to dissolve under the given biological conditions. Moreover, it has become known that such ceramics are covered by a layer of albumin or sugar molecules which form an additional protection layer and carry out a connection function to the surrounding tissue.

As a result of the blind pocket disposed at the end of the post-like part pointing into the mouth, whch serves for the fastening of a crown, bridge or superstructure, the height of the part projecting over the mucous membrane can be kept as small as possible, i.e., just as high as needed by the ring of bioinert ceramics for the production of the annular groove.

Thus the invention implant fulfills the main object set out above since it is embedded directly in bone, i.e., motionless in the jaw bone, and since no kind of irritation can occur in the area of the extension through the mucous membrane as a result of metal ions going into solution.

DETAILED DESCRIPTION OF THE INVENTION

Preferred embodiments of the implant of the invention are described on the basis of the three Figures.

Figure 1:
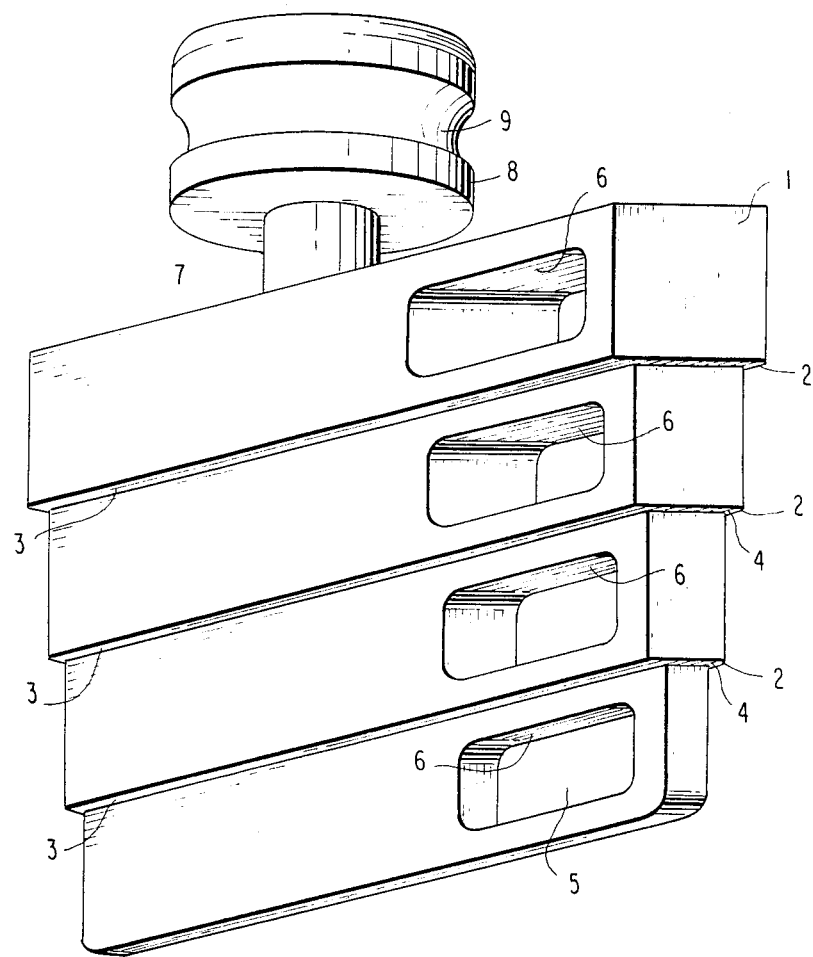
FIG. 1 is a perspective view of one embodiment of the invention implant.
Figure 2:
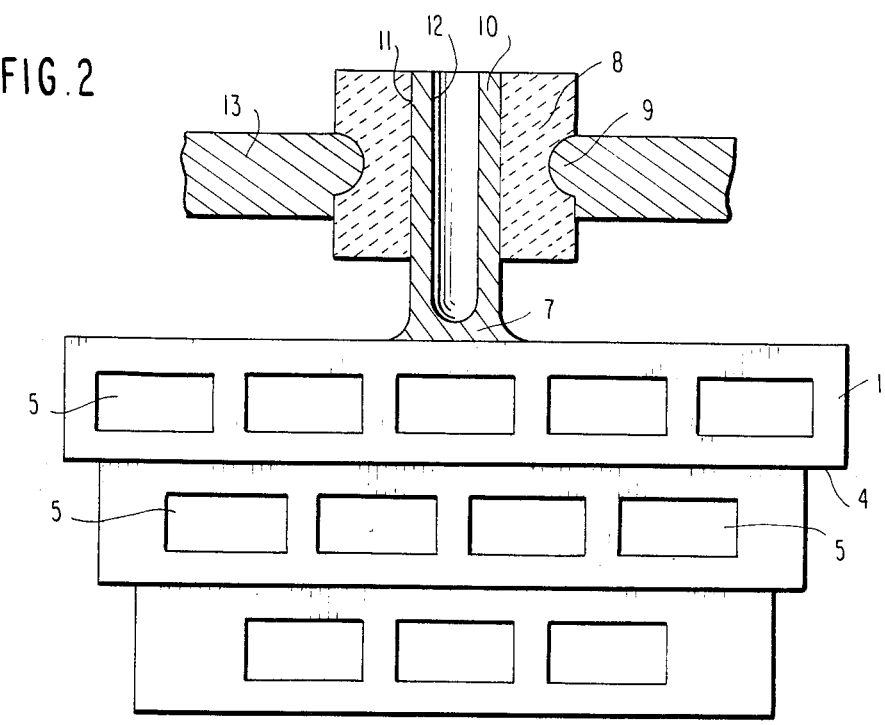
FIG. 2 is a front elevational view, partially cutaway, of the invention implant of FIG. 1.

FIG. 1 shows an implant of the invention, in perspective. FIG. 2 shows such an implant in cut, whereby the cut plane lies about in the plane of symmetry of the leaf-shaped part of the implant in parallel to the largest surface of the leaf.

In FIG. 1, numeral 1 signifies the leaf-shaped part of the implant, numerals 2 are the steps and numerals 3 are the step surfaces. The corresponding step surfaces at the narrow sides of the leaf-shaped part are indicated by numerals 4. In the particular embodiment shown in FIG. 1, the implant has perforations 5, which have limiting surfaces 6 oriented perpendicularly to the plane of the leaf. Numeral 7 designates the post-like part. In the area of the extension through mucous membrane 13, post-like part 7 is surrounded by ring 8 of bioinert ceramic, which on its outside has annular groove 9.

In FIG. 2, the implant is cross-section, note cylindrical section 10 of post-like part 7 which contains blind hole 12A1.

The border surface between cylindrical section 11 of post-like part 7 and ring 8 of bioinert ceramic is designated by numeral 11. The "active soldering" method is provided for the bacteria-tight connection along border surface 11. In the technique, which deals with the connecting of ceramic with metal parts, one understands by "active soldering" those solderings in the case of which the connection between the two parts takes place without prior metallization of the ceramic. This soldering technique constitutes the state of the prior art in this special field.

Figure 3:
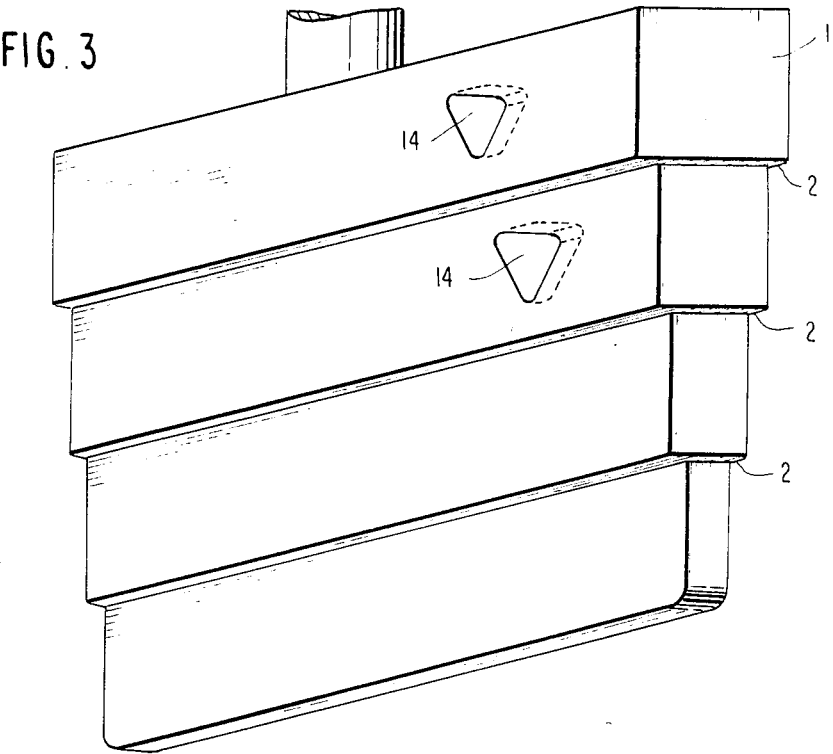
FIG. 3 is a partial perspective view of another embodiment of the invention tooth implant.

FIG. 3 shows leaf-shaped part 1 of FIG. 1 which has lacuna-like indentations 14 instead of penetrations 5 shown in FIG. 1.

What is claimed is:

1. Implant made of a metal which is corrosion resistant in the body, consisting of an essentially leaf-shaped part to be inserted into the jaw bone, a post part for leading from the jaw bone right through the mucous membrane into the mouth cavity and means, provided at the end of the post part adapted to point into the mouth cavity, for attachment of a superstructure, characterized in that the leaf-shaped part has steps, the step surfaces of which are diospsed away from the post part and accordingly point into the jaw bone in use, that the post part is cylindrical in the area for extending through the mucous membrane and in such area carries a ring of bioinert ceramic, which has an annular groove on its outer surface, and that the means for attaching said superstructure consists of a blind hole disposed in the post part.

2. Implant as claimed in claim 1 wherein the leaf-shaped part has perforations, and the perforations have sides which are disposed perpendicularly to the largest surface of the leaf.

3. Implant as claimed in claim 2 wherein the perforations have a rectangular cross section and the two parallel sides of the rectangle are oriented in parallel to the step surfaces.

4. Implant as claimed in claim 1 wherein the connection between the post part and the ring of bioinert ceramic had been produced by the active soldering method.

5. Implant as claimed in claim 1 wherein the surface of the ceramic is polished in the area of the annular groove.

6. Implant as claimed in claim 1 wherein the ring of bioinert ceramic consists of dense aluminum oxide ceramic.

7. Implant as claimed in claim 1 wherein the leaf-shaped part has lacuna-like indentations.

8. Implant as claimed in claim 1 wherein the blind hole is oriented on the vertical axis of the post part and exits on the top surface of the post part.

9. Implant as claimed in claim 1 wherein the leaf-shaped part has perforations, the perforations have sides which are disposed perpendicularly to the largest surface of the leaf, the connection between the post part and the ring of bioinert ceramic had been produced by the active soldering method, the surface of the ceramic is polished in the area of the annular groove, the ring of bioinert ceramic consists of dense aluminum oxide ceramic, the leaf-shaped part has lacuna-like indentations, and the blind hole is oriented on the vertical axis of the post part and exits on the top surface of the post part.

10. Implant as claimed in claim 9 wherein the perforations have a rectangular cross section and the two parallel sides of the rectangle are oriented in parallel to the step surfaces.

11. Implant as claimed in claim 1 wherein said metal is selected from the group consisting of titanium, tantalum and niobium.

12. Implant as claimed in claim 1 wherein said superstructure is a crown.

13. Implant as claimed in claim 1 wherein the post part is cylindrical shaped.

14. Implant as claimed in claim 1 wherein said superstructure is a bridge.

* * * * *